United States Patent [19]
Golub

[11] Patent Number: 5,857,975
[45] Date of Patent: Jan. 12, 1999

[54] METHOD AND APPARATUS FOR NON-INVASIVE, CUFFLESS CONTINUOUS BLOOD PRESSURE DETERMINATION

[75] Inventor: Howard L. Golub, Chestnut Hill, Mass.

[73] Assignee: DxTek, Inc., Chestnut Hill, Mass.

[21] Appl. No.: 80,510

[22] Filed: May 18, 1998

Related U.S. Application Data

[63] Continuation-in-part of Ser. No. 729,445, Oct. 11, 1996.
[51] Int. Cl.$^6$ .................................................. A61B 05/00
[52] U.S. Cl. ........................ 600/485; 600/490; 600/494; 600/500; 600/480; 600/503
[58] Field of Search .................................... 600/480, 485, 600/490, 493–503

[56] References Cited

U.S. PATENT DOCUMENTS

| | | | |
|---|---|---|---|
| 4,869,262 | 9/1989 | Orr et al. | 600/485 |
| 4,907,596 | 3/1990 | Schmid et al. | 600/485 |
| 5,368,040 | 11/1994 | Carney | 600/485 |

*Primary Examiner*—Robert L. Nasser
*Attorney, Agent, or Firm*—Choate, Hall & Stewart; Sam Pasternack

[57] ABSTRACT

Arterial blood pressure of a subject is determined by detecting the EKG for the subject and selecting a fiducial point on the EKG during a pulse. Apparatus is provided for monitoring blood volume versus time at a selected location on the subject's body such as a fingertip. A time difference between the occurrence of the selected fiducial point on the EKG and a selected change in blood in volume at the selected body location is determined. This time difference depends on the arrival time of the pulse at the distal location in addition to the shape of the blood volume versus time curve. Heart rate is determined from the EKG. The arterial pressure is computed from pulse arrival time, volumetric wave shape and instantaneous heart rate for each pulse. It is preferred that the fiducial point on the EKG be an R-wave. A suitable method for determining change in blood volume utilizes photoplethysmography. Methods are disclosed for determining diastolic pressure, systolic and mean arterial pressure. In another aspect, artifact detection and rejection enabled. The invention provides for a continuous measure of blood pressure in a non-invasive, cuffless manner.

4 Claims, 1 Drawing Sheet

METHOD AND APPARATUS FOR NON-INVASIVE, CUFFLESS CONTINUOUS BLOOD PRESSURE DETERMINATION

This application claims priority from and is a continuation-in-part of U.S. Ser. No. 08/729,445, filed Oct. 11, 1996.

BACKGROUND OF THE INVENTION

Several distinct arterial blood-pressure parameters yield medically useful information, among them pressure at systole, pressure at diastole, mean arterial pressure, pulse pressure, and continuous arterial pressure. The traditional ways of measuring these may be categorized as follows: sphygmomanometry (cuff measurement), automated sphygmomanometry, and indwelling arterial-line transduction (A-line).

The importance of continuous arterial blood pressure as a medical indicator has spurred the development of new methods of measuring it. These include external pressure transduction, photoplethysmography, and pulse-wave transit timing. To date these latter methods have been used mainly experimentally.

Sphygmomanometry, the most widely used traditional method, gives pressure at systole and pressure at diastole. The automated cuff uses a machine-actuated pump for cuff inflation, and algorithms and sensors to listen for initial and unrestricted arterial flow. However the cuff methods restrict blood flow during each measurement so they are unsuited to continuous use, and the determinations of blood pressure made by many automatic cuff systems fail to meet accuracy standards. The cuff also produces discomfort to the patient, which can influence blood pressure readings.

A-lines, which are used when continuous measurement is necessary, are reasonably accurate during periods free from signal artifact, from sources such as line-crimping, blood-clotting, and contact between the indwelling transducer and the arterial wall. However the transducer needs to be inserted surgically, and can cause thrombosis and infection. Because the method necessitates a surgical procedure, it is used sparingly, and frequently not recommended for use even when continuous pressure measurement would otherwise be desirable.

The experimental methods noted all attempt to circumvent the drawbacks of the A-line by measuring continuous blood pressure externally. Both direct external pressure sensing and indirect calculation methods have been devised.

The direct non-invasive methods use external pressure transduction. A pressure transducer is placed against an artery that lies just beneath the skin, such as the radial artery, and by pushing against the arterial wall senses pressure mechanically. However, because the transducer is sensing force, it is extremely subject to mechanical noise and motion artifact. Continuous measurement is problematical in that the transducer impedes blood flow. Difficulty also arises in keeping the transducer positioned properly over the artery. Thus, indirect-measurement methods have been considered.

Pulse-wave transit-time measurement is an indirect way of inferring arterial blood pressure from the velocity of the pulse wave produced at each heart cycle. however, though the velocity is related to blood pressure, the methods devised to date assume that the relationship is linear, and even if that were the case, it is probable that transit time by itself provides too little information about the pulse wave to permit the determination of blood pressure accurately. Another shortcoming of the method is that it is incapable of giving pressures at both systole and diastole, which many medical practitioners find useful.

Photoplethysmography, a technique of tracking arterial blood-volume and blood oxygen content, gives rise to the other indirect way of inferring blood pressure continuously. However, the methods based on it derive information from the volumetric data as though it were the same as blood pressure; that is, they assume that blood-pressure and blood-volume curves are similar—which is true sometimes but not in general. Furthermore, photoplethysmographic measurements are made at bodily extremities such as the earlobe or finger, and blood pressure observed at the body's periphery is not generally the same as from more central measurements.

Because the insertion of an A-line is frequently judged to be too invasive a procedure to undertake in order to determine blood pressure, and no practical non-surgical method of continuous measurement has yet supplanted it, the need for one remains.

SUMMARY OF THE INVENTION

In one aspect, the method according to the invention for determining arterial blood pressure in a subject includes detecting an EKG signal for the subject. A fiducial point on the EKG signal is selected and the blood volume versus time wave shape at a selected location on the subject's body is monitored. Instantaneous heart rate is determined from the EKG signal and arterial pressure is calculated from the instantaneous heart rate and the blood volume versus time wave shape. In one embodiment, the fiducial point is the R-wave and arterial pressure is calculated utilizing a selected change in blood volume from the blood volume versus time wave shape. It is preferred that the selected change in blood volume be in the range of 20% to 80% on the upslope on the wave shape. It is more preferred that the selected change in blood volume is in the range of 40% to 60%. The most preferred selected change in blood volume is approximately 50% on the upslope of the volume waveform. It is preferred that the selected body portion is a distal location such as a fingertip.

In another aspect, the method according to the invention for determining arterial blood pressure in a subject includes detecting an EKG for the subject and selecting a fiducial point on the EKG during the pulse period. Blood volume versus time is monitored at a selected location on the subject's body. The time difference between occurrence of the selected fiducial point on the EKG and occurrence of a selected change in blood volume at the selected body location is determined. Heart rate is determined from the EKG and arterial pressure is computed based on the time difference and heart rate. In a preferred embodiment, the fiducial point is the R-wave and the body portion is a distal location such as a fingertip. A preferred method for monitoring blood volume utilizes photoplethysmography. The computed arterial pressure may be diastolic pressure, systolic pressure, or mean arterial pressure.

In another aspect, apparatus according to the invention for determining arterial blood pressure includes EKG apparatus for detecting electrical activity of the heart. Apparatus responsive to change in blood volume may include photoplethysmography apparatus. Outputs from the EKG apparatus and the blood volume monitoring apparatus are introduced into a signal processor or computer which computes arterial blood pressure.

In yet another aspect, the signal processing and computing apparatus is adapted to detect artifacts in the blood pressure measurement and to reject such artifacts. These techniques allow for the reliable assessment of the confidence of the blood pressure calculation for each pulse. The techniques disclosed herein provide a much more reliable measure of blood pressure during times of good input signal and informs the user that there are no available measures during times of poor input signal quality.

The present invention provides an improved method and apparatus for measuring arterial blood pressure continuously, non-invasively, and without the use of a blood pressure cuff. Because of the automated artifact detection and rejection, a reliable assessment of the confidence of the blood pressure computation for each pulse can be made.

DESCRIPTION OF THE PREFERRED EMBODIMENT

Figure 1:
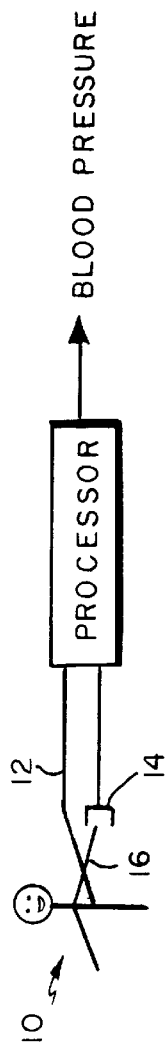
FIG. 1 is a schematic illustration of the apparatus of the present invention.

The physics of wave propagation in elastic tubes is an important factor to understand the underlying concept of the present invention. The simplest equation for the velocity of propagation of a pressure pulse in an elastic tube was first described by Moens-Kortweg who from experimental evidence and theoretical grounds established the formula $$c = \sqrt{\frac{Eh}{2R\delta}}$$

where c is the wave velocity, E and h are Young's modulus and thickness of the arterial wall, $\delta$ the density of the fluid and R the mean radius of the tube.

To eliminate the experimental difficulties of measuring the wall thickness and Young's modulus the Moens-Kortweg equation was modified by Bramwell and Hill (1922) so that the elastic behavior of the tube was expressed in terms of its pressure-volume distensibility. The formula can then be reduced to $$c = \sqrt{\frac{V}{\delta(\partial V/\partial P)}} = \sqrt{\frac{V\partial P}{\delta \partial V}}$$

or $$\Delta P \propto c^2 \left(\frac{\Delta V}{V}\right)$$

where V is the initial volume of the artery, $\Delta V$ is the change in volume resulting in the pressure pulse $\Delta P$ and c is the pulse wave velocity.

The problem then involves determining a non-invasive way of measuring both the pulse wave velocity, and percent change in arterial volume. In order to accomplish this, we have chosen to use the standard EKG signal and any stable measure of blood volume versus time (such as photoplethysmography in the preferred embodiment).

The method of utilizing the EKG signal and blood volume versus time signals include first measuring the $T_{R_{13}\_50(i)}$ (duration of R-wave on EKG to 50% point on volume versus time up-slope) for the i'th pulse. This duration is the sum of the time between the R-wave and the arrival of the pulse 0% point ($T_{R\_0(i)}$) added to the duration of the pulse 0% point to the 50% point on the up-slope ($T_{0\_50(i)}$). The inverse of $T_{R\_0(i)}$ is proportional to the pulse velocity as defined above (or c $\propto 1/T_{R\_0(i)}$) and $T_{0\_50(i)}$ is more related to $\Delta V$ and V. Therefore the inverse of the sum of these (or the measure $$v_{p(i)} = \frac{1}{T_{R\_50(i)}},$$

which is equal to $$\frac{1}{[T_{R\_0(i)} + T_{0\_50(i)}]})$$

is a measure that is related to c, $\Delta V$ and V.

Then, the combined pulse velocity measure for the i'th pulse ($v_{p(i)}$) is therefore defined as the inverse of $T_{R\_50(i)}$ and the combined pulse velocity squared ($v_{p(i)}^2$) is obtained by simply squaring $v_{p(i)}$. Also the instantaneous R—R interval and thereby instantaneous heart rate for the i'th pressure pulse ($RR_i$ and $IHR_{(i)}$ respectively) are determined and used in the calculation of diastolic, systolic and mean pressures for the i'th pulse ($P_{D(i)}$, $P_{S(i)}$ and $P_{M(i)}$ respectively). The theoretical basis for the importance of the R—R interval or IHR in the calculation of diastolic pressure can be summarized as follows. The diastolic pressure is defined as that arterial pressure that exists at the end of the diastolic pressure decay. This exponential diastolic pressure decay starts at the closure of the aortic valve, and ends at the opening of the aortic valve. The pressure decay rate depends on a variety of factors, including the aortic pressure built up during systole, and the systemic arterial impedance (related to the stiffness of the walls of the arterial system, especially the arteriole). For a given individual, the pressure this decay falls to for any given heart beat (or diastolic pressure) is therefore related to the duration this decay is allowed to continue. This duration of decay for any given pulse is directly proportional to the instantaneous R—R interval or inversely proportional to the IHR of that pulse. Therefore, the shorter the decay duration (higher IHR), the higher the diastolic pressure is expected to be, and the longer the decay duration (lower IHR), the lower the diastolic pressure is expected to be. In summary the equations for the calculation of pressures for the i'th pressure pulse are as follows:

$$IHR_{(i)} = 1/RR_{(i)}$$

$$v_{p(i)}^2 = (1/T_{R\_50(i)}) * (1/T_{R\_50(i)})$$

$$P_{D(i)} = (K_{Dv} * v_{p(i)}^2) + (K_{Dihr} * IHR_{(i)}) + K_{Dcal}$$

$$P_{S(i)} = (K_{Sv} * v_{p(i)}^2) + K_{Scal}$$

$$P_{M(i)} = (P_{S(i)} - P_{D(i)}) * \frac{1}{3} + P_{D(i)}$$

In these equations, $K_{Dv}$, $K_{Dihr}$ and $K_{Sv}$ are constants that in the preferred embodiment are equal to 2.5, 0.5 and 5.0 respectively, and where $K_{Dcal}$ and $K_{Scal}$ are calibration constants. $P_{D(i)}$, $P_{S(i)}$ and $P_{M(i)}$ are diastolic, systolic and mean arterial pressure respectively.

Figure 2:
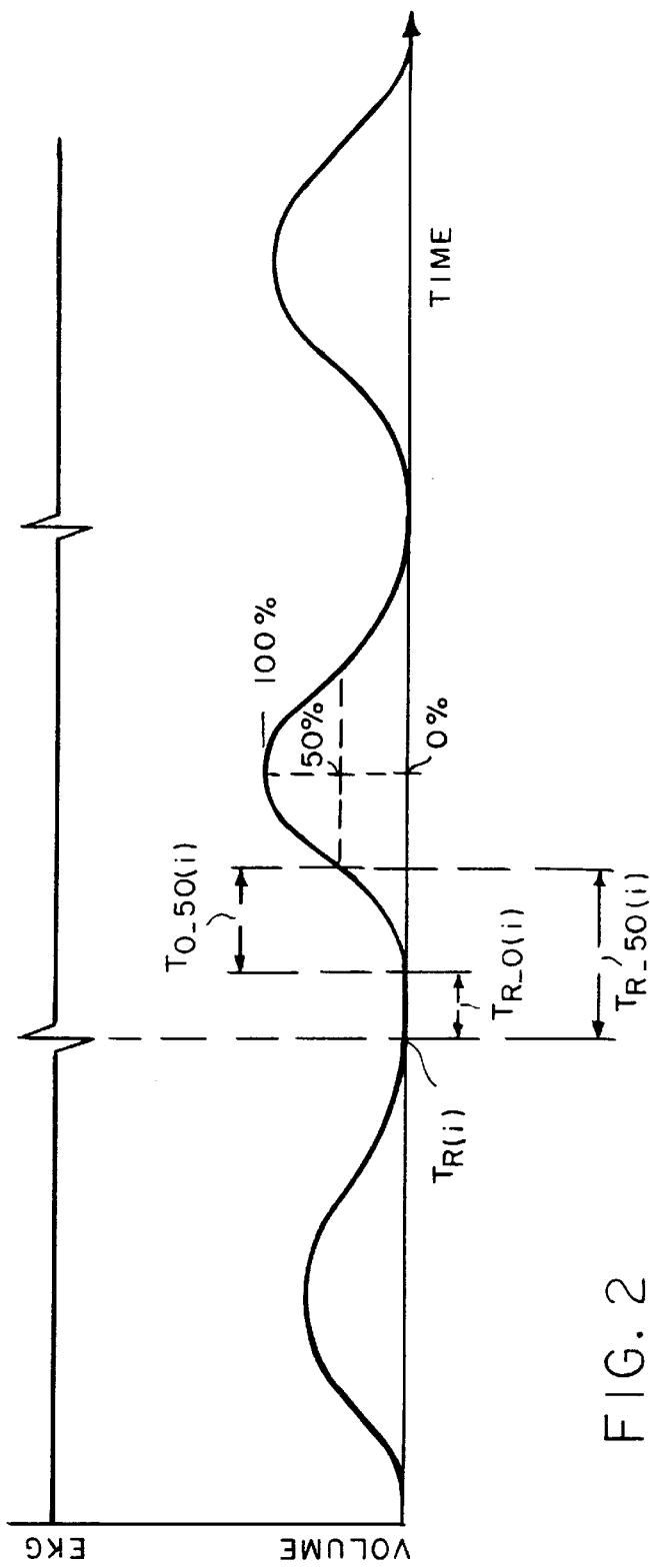
FIG. 2 is a graph of EKG and blood volume versus time.

The practice of the present invention will be described in conjunction with the figures. In FIG. 1 a human subject 10 is monitored by EKG leads represented generally at 12. Those skilled in the art recognize that multiple leads are typically utilized for measuring the EKG. Photoplethysmography apparatus 14 monitors blood volume at a fingertip 16 of the subject 10. The outputs from the EKG apparatus 12 and photoplethysmography apparatus 14 are processed in a computer or signal processor 18 and produces as an output blood pressure which, as discussed above, may be diastolic pressure, systolic pressure or mean arterial pressure for each pulse. With reference to FIG. 2, the processor 18 detects the R-wave arrival. Thereafter, the blood volume measuring apparatus 14 detects the onset of a change in volume at time $T_{R\_0(i)}$ and determines the time when volume has reached the 50% ($T_{0\_50(i)}$) point on the volume versus time upslope. As can be seen in FIG. 2, the time from the arrival of the pulse zero percent point ($T_{R\_0(i)}$) to the 50% point on the upslope ($T_{0\_50(i)}$) depends on the shape of the volume versus time curve. Because the present invention utilizes both the time from R-wave arrival to the zero percent volume change point, and from the zero percent volume change point to the 50% point, pressure determinations are more accurate than in the prior art in which either pulse arrival time or wave shape was utilized but not both in combination as in the present invention.

Another aspect of the invention includes methods for automated artifact detection and rejection thereby providing a reliable assessment of the confidence of each blood pressure calculation for each pulse. These artifact rejection methods include the calculation of two additional variables for each pulse. For the i'th pulse they are as follows:

$$qv_{p(i)}^2 = ({}^i v_{p(3)}^2 - {}^i v_{p(1)}^2)/{}^i v_{p(2)}^2$$

where ${}^i v_{p(1)}^2$ is obtained by sorting five consecutive $v_p^2$ terms $\{v_{p(i-2)}^2, v_{p(i-1)}^2, v_{p(i)}^2, v_{p(i-1)}^2, v_{p(i+2)}^2\}$ and is the second lowest value, ${}^i v_{p(2)}^2$ is the median of the values, and ${}^i v_{p(3)}^2$ is the second highest of the values. And $$diffv_{p(i)}^2 = v_{p(i)}^2 - v_{p(i-1)}^2$$

The algorithm for the detection of whether the i'th pulse is artifact involves testing if these variables are above predetermined thresholds. In this preferred embodiment, the test includes whether either $$qv_{p(i)}^2 > THRESH\_qv$$

$$diffv_{p(i)}^2 > THRESH\_diffv$$

where the preferred values of THRESH_qv=0.8 and THRESH_diffv=8.0. More specifically, these variables are used in addition to the following others to determine the $P_{D(i)}$ calculation artifact. The algorithm includes whether:

$$qv_{p(i)}^2 > THRESH\_qv$$

or $$P_{D(i)} < PD\_TOOLOW$$

or $$P_{D(i)} > PD\_TOOHIGH$$

or $$P_{D(i)} > P_{S(i)}$$

where in the preferred embodiment, PD_TOOLOW=30 and PD_TOOHIGH=150. If any of the above are true then it is deemed that the diastolic pressure for the i'th pulse ($P_{D(i)}$) is not evaluable.

Specifically, and in like manner, the artifact determination for $P_{S(i)}$ calculation includes whether:

$$qv_{p(i)}^2 > THRESH\_qv$$

or $$diffv_{p(i)}^2 > THRESH\_diffv$$

or $$P_{S(i)} < PS\_TOOLOW$$

or $$P_{S(i)} > PS\_TOOHIGH$$

or $$P_{D(i)} > P_{S(i)}$$

where in the preferred embodiment, PS_TOOLOW=50 and PS_TOOHIGH=200. If any of the above are true then it is deemed that the systolic pressure for the i'th pulse ($P_{S(i)}$) is not evaluable.

Finally and specifically, the determination if the $P_{M(i)}$ calculation would result in artifact for the i'th pulse if:

$P_{D(i)}$ is not evaluable or $P_{S(i)}$ is not evaluable and if either is true, then the mean pressure for the i'th pulse is deemed to be not evaluable.

What is claimed is:

1. Method for determining systolic blood pressure in a subject comprising:
   detecting an EKG for the subject;
   selecting a fiducial point on the EKG during a pulse;
   monitoring blood volume versus time at a selected location on the subject's body;
   determining time difference between occurrence of the selected fiducial point and occurrence of a selected change in blood volume at the selected body location;
   determining heart rate from the EKG; and
   computing systolic pressure based on the time difference and heart rate, wherein systolic pressure, $P_{S(i)}$, is determined by computing $$P_{S(i)} = (K_{Sv} * v_{p(i)}^2) + K_{Scal}$$

wherein $K_{Sv}$ is a constant; and $K_{Scal}$ is a calibration constant; $v_{p(i)}$ is the pulse velocity; and i refers to the $i^{th}$ pulse.

2. The method of claim 1 wherein $K_{Sv}$ is approximately 5.0.

3. Method for determining mean arterial blood pressure in a subject, comprising:
   detecting an EKG for the subject;
   selecting a fiducial point on the EKG during a pulse;
   monitoring blood volume versus time at a selected location on the subject's body;
   determining time difference between occurrence of the selected fiducial point and occurrence of a selected change in blood volume at the selected body location;
   determining heart rate from the EKG; and
   computing mean arterial pressure based on the time difference and heart rate, wherein mean arterial pressure, $P_{M(i)}$, is determined by computing $$P_{M(i)} = ((K_{Sv} * v_{p(i)}^2) + K_{Scal} - (K_{Dv} * v_{p(i)}^2) + (K_{Dihr} * IHR_{(i)}) + K_{Dcal}) * \tfrac{1}{3} + (K_{Dv} * v_{p(i)}^2) + (K_{Dihr} * IHR_{(i)}) + K_{Dcal}$$

wherein $T_{R\_50(i)}$ is the time difference between occurrence of the selected fiducial point and a change in blood volume at the selected body location; $K_{Dv}$, $K_{Dihr}$ and $K_{Sv}$ are constants and $K_{Dcal}$ and $K_{Scal}$ are calibration constants; $IHR_{(i)}$ is the instantaneous heart rate; $v_{p(i)}$ is the pulse velocity; and i refers to the $i^{th}$ pulse.

4. The method of claim 3, wherein $K_{Dv}$ is approximately 2.5, $K_{Dihr}$ is approximately 0.5, and $K_{Sv}$ is approximately 5.0.

* * * * *